United States Patent [19]

Grossman et al.

[11] Patent Number: 4,921,525
[45] Date of Patent: May 1, 1990

[54] THIODIAZOLYLUREA-CONTAINING AGENT FOR DEFOLIATING PLANTS

[75] Inventors: Klaus Grossman, Neuhofen; Johann Jung, Limburgerhof; Guenter Schulz, Ludwigshafen; Hubert Sauter, Mannheim; Peter Hofmeister, Neustadt; Wolfgang Tuerk, Ludwigshafen, all of Fed. Rep. of Germany

[73] Assignee: BASF Aktiengesellschaft, Ludwigshafen, Fed. Rep. of Germany

[21] Appl. No.: 258,058

[22] Filed: Oct. 14, 1988

Related U.S. Application Data

[63] Continuation of Ser. No. 35,892, Apr. 8, 1987, abandoned.

[30] Foreign Application Priority Data

Apr. 16, 1986 [DE] Fed. Rep. of Germany ....... 3612830

[51] Int. Cl.$^5$ ............................................ A01D 43/28
[52] U.S. Cl. ........................................... 71/73; 71/90
[58] Field of Search ............................................. 71/73

[56] References Cited

U.S. PATENT DOCUMENTS

| | | | |
|---|---|---|---|
| 3,972,706 | 8/1976 | Arnold | 71/90 |
| 3,990,879 | 11/1976 | Soper | 71/66 |
| 4,412,079 | 10/1983 | Cebalo et al. | 548/141 |

FOREIGN PATENT DOCUMENTS

| | | |
|---|---|---|
| 1923939 | 11/1969 | Fed. Rep. of Germany . |
| 554886 | 10/1974 | Switzerland . |
| 1195672 | 6/1970 | United Kingdom . |
| 1230432 | 5/1971 | United Kingdom . |
| 1266542 | 3/1972 | United Kingdom . |

OTHER PUBLICATIONS

J. Med. Chem. (1979), vol. 22, No. 1, pp. 28-32.
J. Med. Chem. (1972), vol. 15, No. 10, pp. 1082-1084.

*Primary Examiner*—Catherine L. Mills
*Attorney, Agent, or Firm*—Keil & Weinkauf

[57] ABSTRACT

An agent for defoliating plants, which contains a 1,3,4-thiadiazol-2-ylurea of the formula I

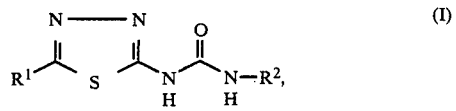

where
$R^1$ is hydrogen or methyl, and
$R^2$ is $C_1$-$C_6$-alkyl, $C_3$-$C_8$-cycloalkyl, $C_2$-$C_4$-alkenyl, $C_3$-$C_6$-alknyl or phenyl which is unsubstituted or substituted by one or 2 chlorine or fluorine atoms, methyl groups, trifluoromethyl groups or methoxy groups, a process for the preparation of the agent, and its use in a method for defoliating plants.

8 Claims, No Drawings

THIODIAZOLYLUREA-CONTAINING AGENT FOR DEFOLIATING PLANTS

This application is a continuation of application Ser. No. 035,892, filed on Apr. 8, 1987, now abandoned.

The present invention relates to thiodiazolylurea-based agents for defoliating plants, a process for the preparation of these agents, and their use in practice.

Special tissue regions at the base of the leaf stalks or flower and fruit stalks are responsible for the separation of plant organs, such as leaves, flowers and fruit, from the plant body. When the separation process begins, the cell walls in the separation zone become soft as a result of increased pectinase and cellulase formation, so that separation of the organ (abscission) becomes possible through mechanical forces, for example by wind or by the weight of the organ itself (Dörffling, Das Hormonsystem der Pflanzen, Georg Thieme Verlag, 1982).

1,2,3-Thiadiazol-5-ylureas are used as synthetic abscission agents (the active ingredient of a commercial product is N-phenyl-N'-(1,2,3-thiadiazol-5-yl)-urea; cf. German Laid-Open Applications DOS 2,506,690 and DOS 2,619,861). However, in the case of the active ingredient used to date, the success of defoliation is highly dependent on the temperature conditions, which restrict its use in areas of cultivation with low temperatures and have a very low adverse effect on the reliability of action, due to the fact that temporary temperature fluctuations cannot be taken into account. 1,3,4-Thiadiazol-2-ylureas have also been disclosed, for example in J. Med. Chem. 22, 28 et seq.; J. Med. Chem. 15, 1082 et seq.; German Laid-Open Application DOS 1,923,939 and Japanese Patent Publication 74-8253. Their use as herbicides, fungicides and pharmacological active compounds is described in these publications. Their use as plant-tolerated abscission agents for controlled induction of the abscission of leaves, flowers or fruit in crop plants, such as cotton, citrus trees, olives and varieties of pip and stone fruit is unknown. Particularly in the case of cotton, there is great commercial interest in abscission agents for facilitating harvesting. Surprisingly, agents which contain, as an active ingredient, an effective concentration of a compound of the formula I

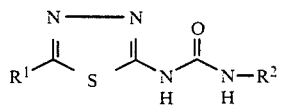
(I)

Where
$R^1$ is hydrogen or methyl and
$R^2$ is $C_1$-$C_6$-alkyl, $C_3$-$C_8$-cycloalkyl, $C_2$-$C_4$-alkenyl, $C_3$-$C_6$-alkynyl or phenyl which is unsubstituted or substituted by one or two chlorine or fluorine atoms, methyl groups, trifluoromethyl groups or methoxy groups, are considerably superior to the known agents based on isomeric ingredients in respect of the intensity of action and the rate of action. Particularly noteworthy is the unexpectedly pronounced defoliation action at relatively low temperatures, which substantially increases the reliability in practice.

The agents are fed to the plants mainly by spraying the leaves. Application may be effected, for example using water as a carrier, by a conventional spraying technique in which the spray liquor is applied at a rate of about 100–1000 l/ha. The agents may be applied by the low volume and ultra low volume methods as well as in the form of microgranules. Because of the good toleration by plants, the application rate of active ingredient can vary greatly. Doses of from 0.01 to 5 kg of active ingredient per hectare are generally sufficient for leaf treatment.

The agents can be obtained simply by mixing an effective amount of a compound of the formula I with suitable liquid or solid carriers and/or adding surfactants.

Examples of suitable liquid carriers are water, aliphatic and aromatic hydrocarbons, such as benzene, toluene, xylene, cyclohexanone, isophorone, dimethyl sulfoxide or dimethylformamide, as well as mineral oil fractions. Examples of suitable solid carriers are mineral earths, such as Tonsil, silica gel, talc, kaolin, Attaclay, limestone and silica, and vegetable products, e.g. meals.

Specific examples of surfactants are calcium ligninsulfonate, polyethylene octylphenyl ether, naphthalenesulfonic acids and their salts, phenolsulfonic acids and their salts, formaldehyde condensates, fatty alcohol sulfates and substituted benzenesulfonic acids and their salts.

The amount of active ingredient or ingredients in the concentrated formulations can vary within wide limits. An agent may contain, for example, about 10–80% by weight of active ingredient, about 30–90% by weight of liquid or solid carriers and, if required, up to 20% by weight of surfactants. It may, if required, be diluted to a suitable concentration for use.

The active ingredients which form the basis can be obtained in a conventional manner, for example by reacting 2-amino-1,3,4-thiadiazole or 2-amino-5-methyl-1,3,4-thiadiazole with a suitable isocyanate:

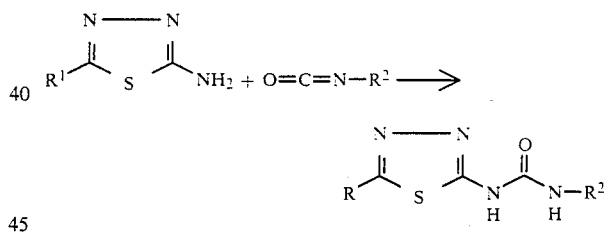

A review of this type of reaction is given in, for example, The Chemistry of cyanates and their thio derivatives, Ed. S. Patei (1977). Examples of compounds of the formula I are listed below, followed by examples of the biological activity of the agents.

The novel agents can be used either alone or as a mixture with other agents or with other active ingredients. If necessary, other defoliants, crop protection agents or pesticides may be added, depending on the effect desired.

TABLE 1

| No. | $R^1$ | $R^2$ | m.p. °C. |
|---|---|---|---|
| 1 | H | $-CH_3$ | |
| 2 | H | $-C_4H_9$ | |
| 3 | H | $-CH(CH_3)_2$ | |
| 4 | H | $-CH_2CH(CH_3)_2$ | 171 |
| 5 | H | Cyclopentyl | 210–12 |
| 6 | H | Cyclohexyl | 211–14 |
| 7 | H | $-CH_2-CH=CH_2$ | 235–36 |
| 8 | H | $-C(CH_3)_2-C\equiv CH$ | 210 |
| 9 | H | $-C_6H_5$ | >230 |
| 10 | H | $-(4-Cl-C_6H_4)$ | |

TABLE 1-continued

| No. | R¹ | R² | m.p. °C. |
|---|---|---|---|
| 11 | H | —(4-CH₃—C₆H₄) | |
| 12 | H | —(2-F—C₆H₄) | >230 |
| 13 | H | —(3-Cl—C₆H₄) | >230 |
| 14 | H | —(3,4-Cl₂—C₆H₃) | >230 |
| 15 | H | —(3-CF₃—C₆H₄) | >230 |
| 16 | H | —(3-OCH₃—C₆H₄) | >230 |
| 17 | —CH₃ | —C₆H₅ | >230 |
| 18 | —CH₃ | —(4-CH₃—C₆H₄) | |
| 19 | —CH₃ | —(4-Cl—C₆H₄) | |
| 20 | —CH₃ | —2(2-F—C₆H₄) | |

USE EXAMPLES

EXAMPLE A

Young cotton plants (Delta Pine variety, development stage: 5–6 developed foliage leaves) were grown under greenhouse conditions (day/night temperature 26°/16° C., relative humidity 50–70%) and the leaves were treated, until dripping wet, with the active ingredients stated below, with the addition of 1% of Citowett, in aqueous solution. Five and seven days after application of the active ingredient, the number of dropped leaves was determined and the degree of defoliation was stated as a percentage of the control.

| Agent containing active compound | converted application rate kg/ha | % Defoliation after 5 days | % Defoliation after 7 days |
|---|---|---|---|
| No. | | | |
| 9 formulated in Tween 85⊕ Final amount 5% by weight | 3 5 | 83 95 | 86 98 |
| 17 formulated in Tween 85⊕ Final amount 5% by weight | 5 | 82 | 84 |
| Comparative agent N—phenyl-N'—(1,2,3-thiadiazol-5-yl)-urea (Commercial product) | 3 5 | 36 41 | 45 54 |
| Untreated | — | 0 | 0 |

⊕Tween 85 is a wetting agent based on polyoxyethylene sorbitan trioleate

EXAMPLE B

Young cotton plants were grown under greenhouse conditions, as described in Example A. After the leaf treatment, as described in Example A, with the agents stated below, the plants were cultivated further in special conditioned rooms at lower temperatures (day/night temperature 22°/13° C.). One week after application of the agents, the number of dropped leaves was determined and the degree of defoliation was stated as a percentage of the control.

| Agent containing active compound | Converted application rate kg/ha | % Defoliation after 1 week |
|---|---|---|
| No. | | |
| 9 formulated in Tween 85+ Final amount 5% by weight | 3 | 65 |
| Comparative agent: N—phenyl-N'—(1,2,3-thiadiazol-5-yl)-urea (Commercial product) | 3 | 9 |
| Untreated | — | 0 |

The results from Examples A and B show that, under certain temperature conditions, the agents according to the invention have a substantially more rapid action than the commercial active ingredient and furthermore exhibit their good action as defoliants even at low temperatures.

We claim:

1. A method of defoliating plants which comprises: applying to the plants an effective amount of a composition containing a liquid or solid carrier and as the active agent at least one 1,3,4-thiadiazol-2-ylurea of the formula I

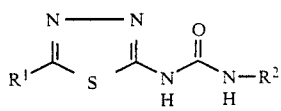

where
R¹ is hydrogen or methyl and
R² is phenyl which is unsubstituted or substituted by one or two chlorine or fluorine atoms, methyl groups, trifluoromethyl groups or methoxy groups.

2. The method of claim 1, wherein the composition contains from 10 to 80% by weight of active agent, from 30–90% by weight of liquid or solid carrier and from 0–20% by weight of surfactant.

3. The method of claim 1, wherein the plants are cotton plants.

4. The method of claim 2, wherein the plants are cotton plants.

5. The method of claim 1, wherein R¹ is hydrogen and R² is unsubstituted phenyl.

6. The method of claim 1, wherein the plants are cotton plants and wherein R¹ is hydrogen and R² is unsubstituted phenyl.

7. The method of claim 1, wherein R¹ is methyl and R² is unsubstituted phenyl.

8. The method of claim 1, wherein the plants are cotton plants and wherein R¹ is methyl and R² is unsubstituted phenyl.

* * * * *